United States Patent
Smith et al.

(10) Patent No.: US 9,329,084 B2
(45) Date of Patent: May 3, 2016

(54) MOVING LASER FOCUS IN A SPECTROMETER

(71) Applicant: Thermo Scientific Portable Analytical Instruments Inc., Tewksbury, MA (US)

(72) Inventors: Malcolm Smith, Winchester, MA (US); Michael Burka, Winchester, MA (US); Stephen McLaughlin, Andover, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 14/080,234

(22) Filed: Nov. 14, 2013

(65) Prior Publication Data
US 2015/0131091 A1    May 14, 2015

(51) Int. Cl.
*G01J 3/44* (2006.01)
*G01J 3/02* (2006.01)
*G01N 21/65* (2006.01)

(52) U.S. Cl.
CPC ............... *G01J 3/0208* (2013.01); *G01N 21/65* (2013.01); *G01N 2201/1056* (2013.01)

(58) Field of Classification Search
CPC ................ G01N 21/65; G01N 21/658; G01N 2021/656; G01J 3/02; G01J 3/44
USPC .................................................. 356/300–334
See application file for complete search history.

(56) References Cited

U.S. PATENT DOCUMENTS

| | | | |
|---|---|---|---|
| 5,719,704 A * | 2/1998 | Shiraishi | G03F 7/70075 355/53 |
| 6,809,812 B2 | 10/2004 | Yin | |
| 7,535,565 B1 | 5/2009 | Viertl et al. | |
| 8,125,637 B2 | 2/2012 | Carron | |
| 2004/0051867 A1 | 3/2004 | Brestel et al. | |
| 2005/0280814 A1 | 12/2005 | Iuliano | |
| 2007/0103682 A1 * | 5/2007 | Yoo | G01J 3/02 356/318 |
| 2007/0263226 A1 * | 11/2007 | Kurtz et al. | 356/492 |
| 2012/0162642 A1 | 6/2012 | Watson | |
| 2012/0223130 A1 | 9/2012 | Knopp et al. | |

FOREIGN PATENT DOCUMENTS

| | | |
|---|---|---|
| EP | 0633541 A1 | 1/1995 |
| WO | 9111290 A1 | 8/1991 |

\* cited by examiner

*Primary Examiner* — Abdullahi Nur
(74) *Attorney, Agent, or Firm* — Ion C. Abraham

(57) ABSTRACT

In an embodiment, an apparatus may include a light source, a beam manipulator, an optical component, an analyzer, and a detector. The light source may generate an incident light at a first frequency. The beam manipulator may include one or more polyhedron-shaped prisms that may deflect the incident light for focus at a plurality of points on a sample. The optical component may collect the deflected incident light, focus the collected deflected incident light at the plurality of points on the sample, and collect scattered light from the sample. The scattered light may include elastic scattered light and/or inelastic scattered light. The inelastic scattered light may have a second frequency that is shifted up or down from the first frequency. The detector may detect the inelastic scattered light and the analyzer may identify a substance contained in the sample based on the detected inelastic scattered light.

11 Claims, 4 Drawing Sheets

MOVING LASER FOCUS IN A SPECTROMETER

BRIEF DESCRIPTION OF THE DRAWINGS

The accompanying drawings, which are incorporated in and constitute a part of this specification, illustrate one or more embodiments described herein and, together with the description, explain these embodiments. In the drawings.

DETAILED DESCRIPTION

Figure 1:
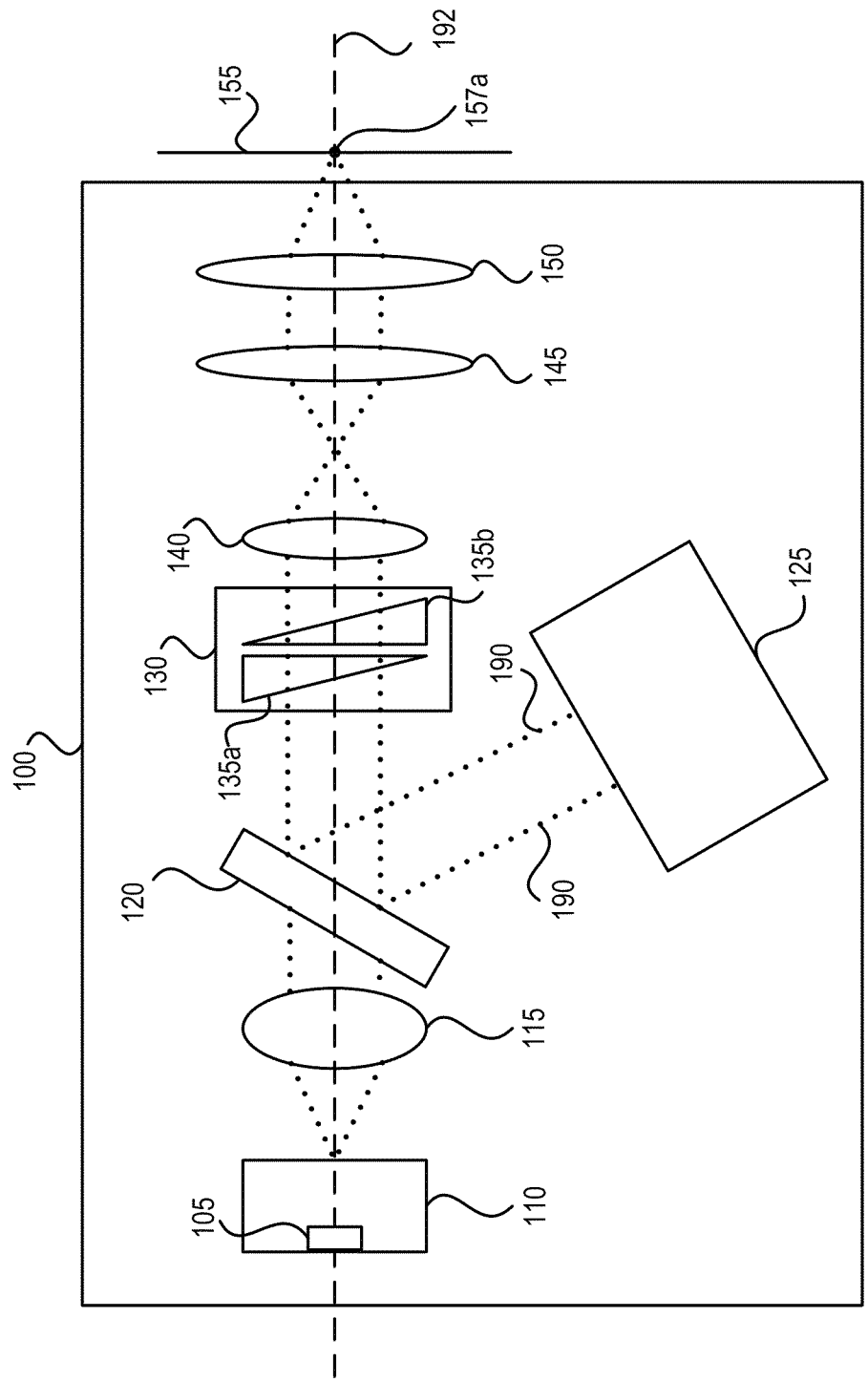
FIG. 1 illustrates a block diagram of an example embodiment of a spectrometer having prisms that may be used to deflect light and an example of a standard focus path for the light.

The following detailed description refers to the accompanying drawings. The same reference numbers in different drawings may identify the same or similar elements. Also, the following detailed description does not limit the invention.

Spectroscopy may be used to observe vibrational, rotational, and/or other low-frequency modes that may be associated with substances that may be contained in a sample. Spectroscopy may involve, for example, (1) focusing an incident light (e.g., a laser beam) on an area of a sample and (2) observing scattering of the incident light. Scattering of the incident light may occur, for example, due to the incident light interacting with molecular vibrations, phonons, or other excitations that may be associated with one or more substances in the sample.

Incident light that has undergone scattering may be referred to as scattered light. Scattered light may include (1) inelastic scattered light which may be incident light that has undergone inelastic scattering (e.g., Raman scattering) and/or (2) elastic scattered light which may be incident light that has undergone elastic scattering (e.g., Rayleigh scattering).

Inelastic scattered light may have a frequency that is different than the frequency of the incident light. The frequency of the inelastic scattered light may be shifted up from the incident light's frequency (e.g., higher in frequency than the incident light's frequency) or shifted down from the incident light's frequency (e.g., lower in frequency than the incident light's frequency). This shift in frequency may occur when the incident light interacts with molecular vibrations, phonons, or other excitations that may be associated with one or more substances. The shift in frequency may be used to identify these substances. Raman spectroscopy may involve observing this shift in frequency to identify and/or quantify the substances.

A Raman spectrometer may be a spectrometer that may employ Raman spectroscopy to identify and/or quantify one or more substances in a sample. The Raman spectrometer may include, for example, a light source, a lens, a filter, an analyzer, and a detector that may be used to identify and/or quantify the substances. The light source may generate an incident light. The generated incident light may be in the form of a laser beam. The lens may collect scattered light from a spot illuminated by the incident light. The collected scattered light may include, for example, inelastic scattered light and elastic scattered light. The collected scattered light may be directed to the filter. The filter may filter out the elastic scattered laser light and pass the inelastic scattered light. The passed inelastic scattered light may be dispersed by the analyzer onto the detector. The detector may detect, for example, one or more frequencies associated with the inelastic scattered light. One or more substances in the sample may be identified and/or quantified by the Raman spectrometer based on, for example, detected frequencies of the inelastic scattered light.

The Raman spectrometer may generate information (e.g., data) associated with the identified and/or quantified substances. The information may include, for example, (1) an identifier that may identify a substance and/or (2) a quantity that may represent a quantity of a substance in the sample. The Raman spectrometer may include provisions for recording (e.g., storing), transferring (e.g., downloading), and/or presenting (e.g., graphing) the generated information.

In identifying and/or quantifying certain substances of a sample using Raman spectroscopy, incident light focused on a particular area of the sample for a particular period of time may cause certain undesirable results. For example, suppose an area of a sample contains a substance that is explosive. Focusing incident light in the form of a laser beam on that area for a period of time may cause the substance to detonate or deflagrate due to, for example, heating effects that may be caused by the laser beam being focused on that area of the sample for that period of time. In certain circumstances, detonation or deflagration of the substance may be considered an undesirable result.

One way to obviate an undesirable result, which may be associated with focusing incident light on a particular area of a sample for a particular period of time, may be to move the incident light on the sample such that the incident light is not focused on a particular area of the sample for a length of time that may cause the undesirable result. For example, in the above example, detonation or deflagration of the substance may be obviated by moving the laser beam to various areas of the sample to prevent heating effects from causing detonation or deflagration of the substance in the sample. The laser beam may be moved, for example, after a predetermined period of time has elapsed or in a continuous manner. The predetermined period of time may be less than an amount of time that may cause detonation or deflagration.

An apparatus that may implement one or more techniques described herein may include a light source, a beam manipulator, and a focusing optical component. The light source may generate an incident light at a first frequency. The beam manipulator may deflect the incident light for focus at a plurality of points on a sample. The beam manipulator may include one or more refracting optical components (e.g., polyhedron prisms) that may deflect the light.

The focusing optical component may collect the deflected incident light and focus the collected deflected incident light at the plurality of points on the sample. The focusing optical component may also collect scattered light from the sample. The collected scattered light may include, for example, elastic scattered light and/or inelastic scattered light. The collected inelastic scattered light may have a second frequency that may be shifted up or down from the first frequency.

The apparatus may include a detector that may have circuitry (e.g., electronic circuitry) for detecting the inelastic scattered light. One or more substances contained in the sample may be identified, for example, by the apparatus based on the detected inelastic scattered light.

The apparatus may include provisions (e.g., motor, drive mechanism, control circuitry) for adjusting positions of the prisms to, for example, obviate one or more undesirable effects that may be caused by focusing the incident light at a particular point on the sample for a particular period of time. The provisions may adjust the position of the prisms after a predetermined period of time has elapsed or in a continuous manner, such as described above.

FIG. 1 illustrates a block diagram of an example embodiment of a spectrometer 100 having prisms that may be used to deflect light and an example of a standard focus path 190 for the light. The spectrometer 100 may be, for example, a Raman spectrometer.

Referring to FIG. 1, the spectrometer 100 may include various components such as, for example, a detector 105, an analyzer 110, a first optical component 115, a filter 120, a light source 125, a beam manipulator 130, a second optical component 140, a third optical component 145, and a fourth optical component 150. Note that spectrometer 100 is an example embodiment of a spectrometer that may implement one or more techniques described herein. Other embodiments of spectrometers that may implement one or more techniques described herein may include more components or fewer components than the components illustrated in FIG. 1.

The detector 105 may include circuitry that may detect inelastic scattered light, such as Raman scattered light. Examples of circuitry that may be included in detector 105 to detect the inelastic scattered light may include, but are not limited to, charge-coupled devices (CCDs), charge-injection devices (CIDs), and/or near-infrared (NIR) active material devices.

The detector 105 may also include circuitry to identify one or more characteristics of the detected inelastic scattered light and generate information (e.g., data) that may represent the one or more identified characteristics. The identified characteristics may include, for example, a frequency, wavelength, wavenumber, and/or intensity of the detected inelastic scattered light. The detector 105 may also include circuitry to identify one or more substances contained in a sample being analyzed by spectrometer 100 based on, for example, the identified characteristics of the detected inelastic scattered light.

The analyzer 110 may include, for example, a dispersing mechanism for resolving the scattered light into its constituent frequencies. Examples of dispersing mechanisms that may be included in analyzer 110 may include, but are not limited to, diffraction gratings, dispersing prisms, and/or bandpass filters. The analyzer 110 may also include, for example, collimating, reflecting, and focusing optics to direct the scattered light onto the detector 105.

The first optical component 115 may include a lens that may collect inelastic scattered light from the filter component 120 and direct the collected inelastic scattered light into the analyzer 110. The collected inelastic scattered light may be dispersed on, for example, circuitry contained in the detector 105 that may be used to detect the inelastic scattered light.

Filter 120 may collect incident light generated by light source 125 and direct the collected incident light along path 190 towards beam manipulator 130. Filter 120 may also collect scattered light from the beam manipulator 130. The collected scattered light may include elastic scattered light and inelastic scattered light. Filter 130 may block (e.g., filter out) the elastic scattered light and pass the inelastic scattered light. The elastic scattered laser light may be blocked, for example, by reflecting the elastic scattered laser light to the light generator 125 along path 190. The inelastic scattered light may be passed, for example, along path 190 towards the first optical component 115. Filter 120 may include, for example, a lens that may block the elastic scattered light and pass the inelastic scattered light. Examples of filters that may be used to implement filter 120 include, but are not limited to, notch filters and edge filters.

Light source 125 may generate an incident light for spectrometer 100. Light source 125 may, for example, include circuitry that may generate the incident light. The incident light may be generated, for example, in the form of a laser beam. The incident light may be generated at various wavelengths. For example, light source 125 may generate the incident light at wavelengths of 532 nanometers (nm), 633 nm, and/or 785 nm. It should be noted that these wavelengths are examples of wavelengths of an incident light that may be generated by light source 125 and that light source 125 may generate an incident light at other wavelengths.

Beam manipulator 130 may direct the incident light along path 190 towards second optical component 140. Beam manipulator 130 may include, for example, prisms 135a-b, which may be used to direct the incident light along path 190. Beam manipulator 130 may direct the incident light along path 190 by positioning prism 135a and/or prism 135b to deflect the incident light and cause the incident light to travel on paths 190a-b towards second optical component 140.

Prism 135a and/or prism 135b may be a transparent object having a plurality of flat surfaces (sometimes called faces) that may be used to refract light. At least two of the flat surfaces of prism 135a and/or prism 135b may be, for example, non-parallel and have an angle between them. Prism 135a and/or prism 135b may be shaped as a polyhedron that may have, for example, flat surfaces and/or straight edges. Prism 135a and/or prism 135b may be wedge-shaped. For example, prism 135a and/or prism 135b may be wedges having two triangular surfaces and three trapezoidal surfaces.

Beam manipulator 130 may include a drive mechanism that may be used to position prism 135a and/or prism 135b. The drive mechanism may include, for example, a motor and one or more components (e.g., gears, belts, shafts). The motor may be used to drive the one or more components. The one or more components may be used to position prism 135a and/or prism 135b. The beam manipulator 130 may also include circuitry (e.g., electronic circuitry) that may be used to control an operation of the drive mechanism.

The prisms 135a-b may be encased in one or more casings that may be contained in beam manipulator 130. The drive mechanism may position prism 135a and/or prism 135b by positioning the one or more casings.

Beam manipulator 130 may also collect scattered light from the second optical component 140. Beam manipulator 130 may direct the collected scattered light towards filter 120 via path 190.

The second optical component 140 may include, for example, a lens that may collect incident light from the beam manipulator 130 and direct the incident light towards the third optical component 145 via path 190. The second optical component 140 may also collect scattered light from third optical component 145 and direct the collected scattered light towards beam manipulator 130 via path 190.

Third optical component 145 may include, for example, a lens that may collect incident light from the second optical component 140 and direct the collected incident light towards the third optical component 145 via path 190. Third optical component 145 may also collect scattered light from the fourth optical component 150 and direct the collected scattered light towards the second optical component 140 via path 190.

Fourth optical component 150 may include, for example, a lens that may collect incident light from the third optical component 145 and focus the collected incident light on sample 155. Fourth optical component 150 may also collect scattered light from the sample 155 and direct the collected scattered light via path 190 towards the third optical component 145.

Operationally, light source 125 may generate an incident light that may follow path 190 towards filter 120. The incident light may be directed by filter 120 towards beam manipulator 130 via path 190. Beam manipulator 130 may collect the incident light from filter 120 and deflect the incident light based on a position of prism 135a and/or a position of prism 135b. Specifically, the incident light may pass through prism 135a and/or prism 135b which may deflect the light based on a position of prism 135a and/or a position of prism 135b. The deflected incident light may be directed by beam manipulator 130 towards second optical component 140 via path 190.

Second optical component 140 may collect the deflected incident light and direct the deflected incident light towards third optical component 145 along path 190. Third optical component 145 may collect the deflected incident light from the second optical component 140 and direct the deflected incident light towards fourth optical component 150 along path 190. Fourth optical component 150 may collect the deflected incident light from the third optical component 145 and focus the deflected incident light at point 157a on sample 155.

The focused incident light may interact with one or more substances on sample 155 and produce scattered light. The scattered light may include, for example, elastic scattered light and/or inelastic scattered light.

Fourth optical component 150 may collect the scattered light and direct the collected scattered light towards third optical component 145 via path 190. Third optical component 145 may collect the scattered light from the fourth optical component 150 and direct the collected scattered light via path 190 towards the second optical component 140. The second optical component may collect the scattered light from the third optical component 145 and direct the collected scattered light towards the beam manipulator 130 via path 190.

The beam manipulator 130 may collect the scattered light and direct the collected scattered light towards filter 120 via path 190. Note that the scattered light may pass through prisms 135a-b where the scattered light may be deflected based on a position of prism 135a and/or a position of prism 135b.

Filter 120 may collect the scattered light from beam manipulator 130 and direct inelastic scattered light, which may be included in the collected scattered light, towards first optical component 115 along path 190. Filter component 120 may also direct elastic scattered laser light, which may be included in the collected scattered light, towards light generator 125. First optical component 115 may collect the inelastic scattered light from filter 120 and direct the collected inelastic scattered light into analyzer 110. Analyzer 110 and detector 105 may process the inelastic scattered light. Processing may include, for example, detecting, identifying and/or measuring substances in sample 155 based on the inelastic scattered light.

Note that FIG. 1 illustrates an optical axis 192 for spectrometer 100. The optical axis 192 may be used as a reference axis for the spectrometer 100. Also note that point 157a is a point on path 190 where the incident light is focused by optical component 150 on sample 155 and that path 190 intersects the optical axis 192 at point 157a. Thus, path 190 may be referred to as a standard focus path for spectrometer 100.

Figure 2:
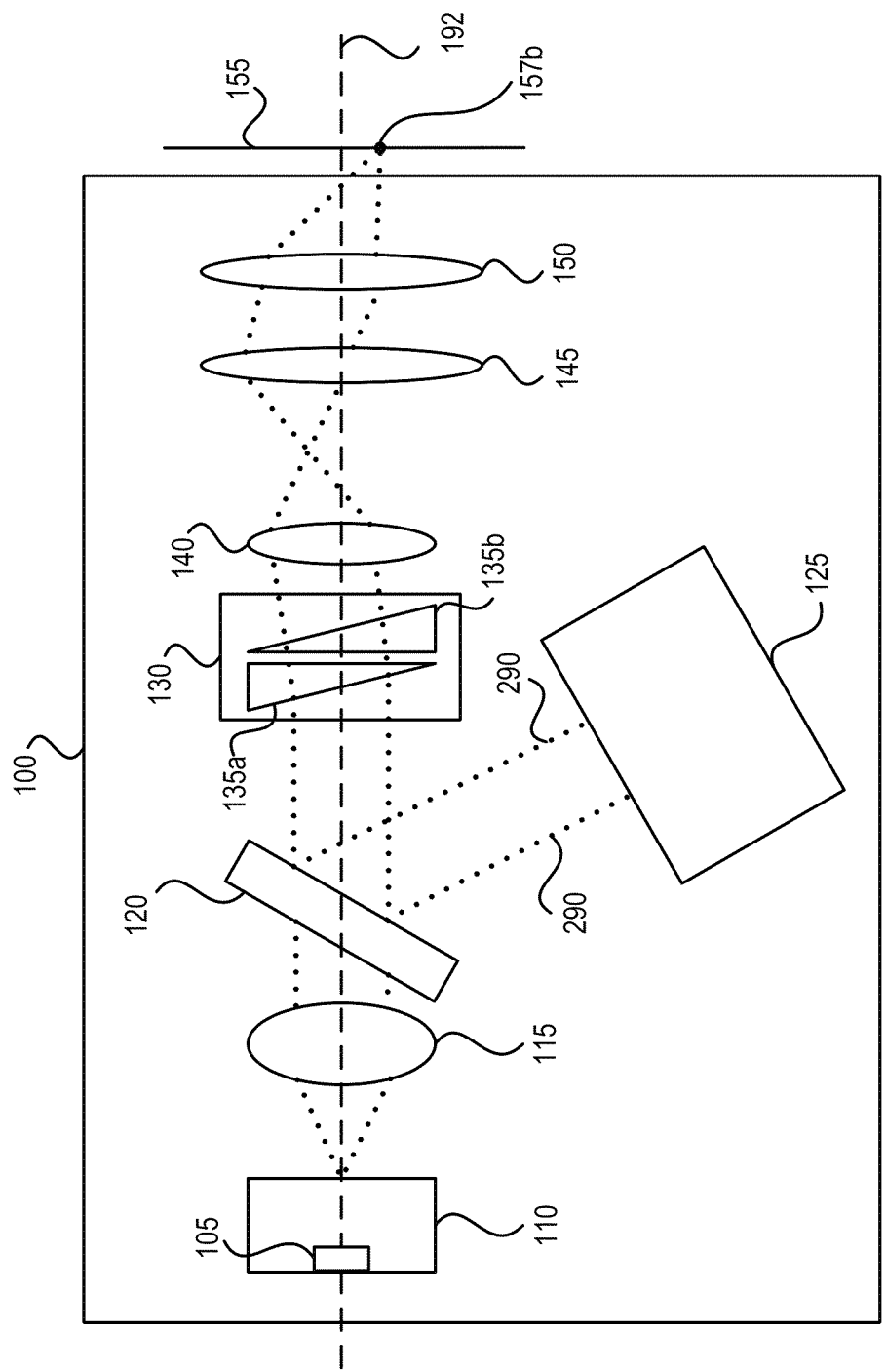
FIG. 2 illustrates a block diagram of an example embodiment of a spectrometer having prisms that may be used to deflect light and an example of an offset focus path for the light.

It should be noted that beam manipulator 130 may also be used to deflect incident light, generated by light source 125, such that the incident light may travel on a path that may be an offset from the standard focus path. This offset path may be referred to as an offset focus path. FIG. 2 illustrates an example offset focus path 290 for light associated with spectrometer 100.

Referring to FIG. 2, beam manipulator 130 may be adjusted to cause a light source generated by light generator 125 to follow offset focus path 290. Specifically, incident light generated by light source 125 may travel via path 290 to beam manipulator 130. Prism 135a and/or prism 135b may be positioned (e.g., rotated) to deflect the incident light along path 290. The deflected light may be collected by second optical component 140 and directed to third optical component 145 via path 290. Second optical component 140 may collect the deflected light and direct the deflected light via path 290 to the third optical component 150 which may focus the light at a second point 157b on sample 155. Note that the second point 157b is at an offset from the standard focus path 190 for spectrometer 100.

Figure 3:
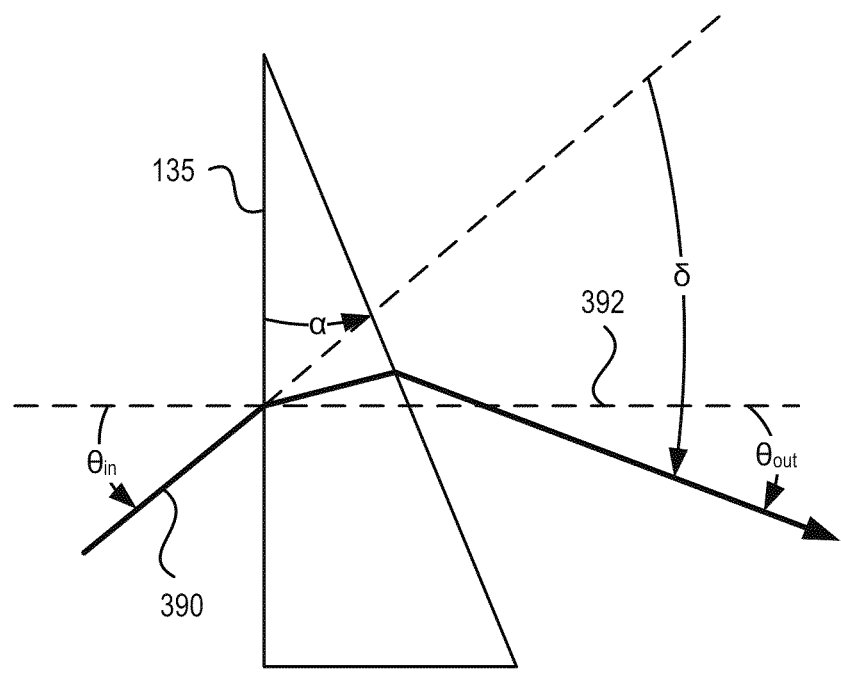
FIG. 3 illustrates an example deflection of light by a prism that may be included in a spectrometer.

As noted above, prism 135a and/or prism 135b may deflect incident light collected by beam manipulator 130 along a particular path. FIG. 3 illustrates an example of this deflection.

Referring to FIG. 3, an axis 392 may provide a reference axis. An example of a reference axis may be an optical axis, such as optical axis 192. Light (e.g., incident light, scattered light) may travel to prism 135 on a path 390 at an angle $\theta_{in}$ with respect to axis 392. The light may be deflected by the prism 135 at a deflection angle $\delta$ and exit the prism 135 at an angle $\theta_{out}$ with respect to axis 392.

For a prism 135 made of a material with a refractive index n and in surrounding air of a refractive index ~1, and has an apex angle $\alpha$, the deflection angle $\delta$ may be determined using the following formula:

$$\delta = \theta_{in} + \arcsin\left(n\,\sin\left(\alpha - \arcsin\left(\frac{1}{n}\sin(\theta_{in})\right)\right)\right) - \alpha$$

For a small apex angle $\alpha$ and small angle $\theta_{in}$, a small angle approximation may be used and the above deflection formula may reduce to, for example, the following formula:

$$\delta \approx (n-1)\alpha$$

Beam manipulator 130 may be used to deflect incident light generated by light source 125 for focus on sample 155 to form one or more patterns on sample 155. The patterns may be generated, for example, by positioning prism 135a and/or prism 135b. An example of a pattern that may be generated by beam manipulator 130 is a roulette curve. Examples of roulette curves that may be generated using beam manipulator 130 include, but are not limited to, epicycloids, hypocycloids, and involutes.

Figure 4:
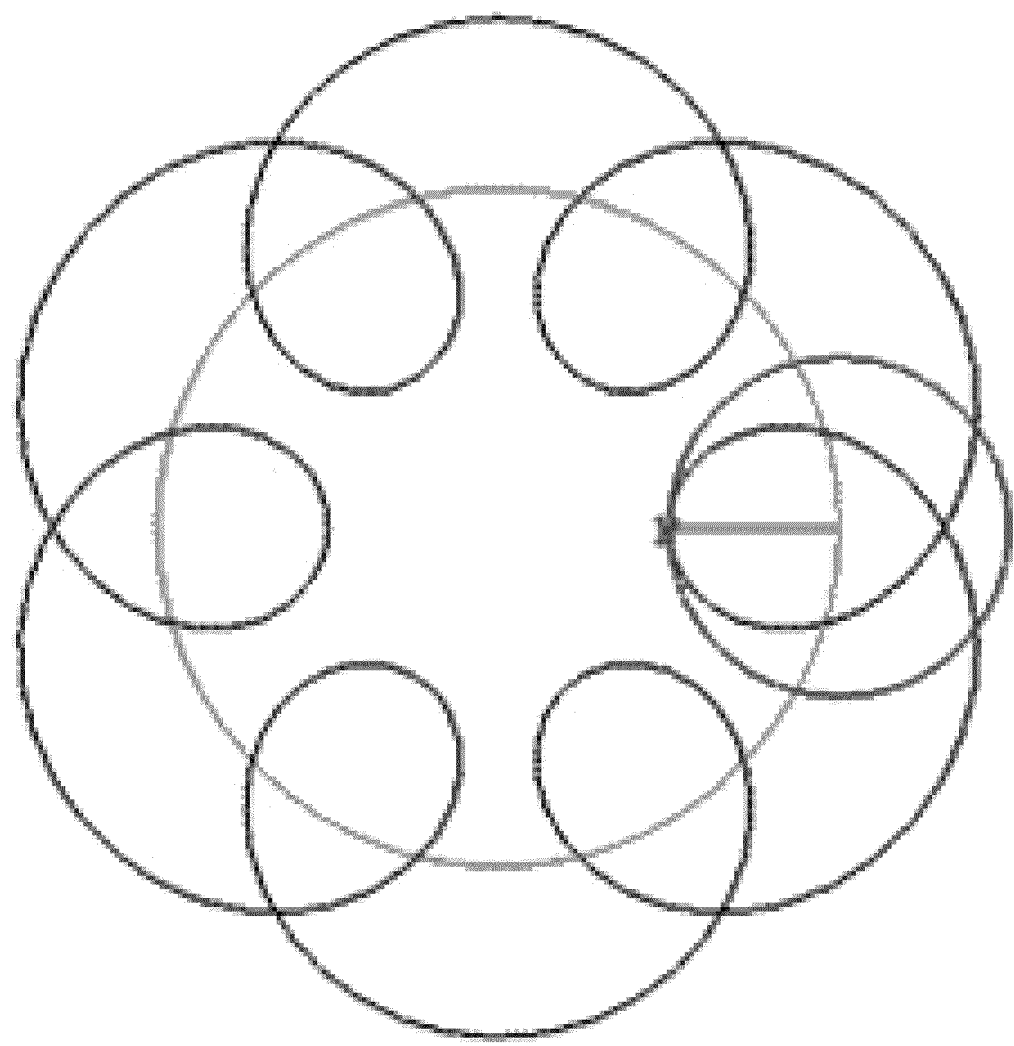
FIG. 4 illustrates an example of a pattern that may be generated on a sample by a spectrometer.

FIG. 4 illustrates an example of a pattern 400 that may be generated on sample 155 using beam manipulator 130. It should be noted that FIG. 4 illustrates an example pattern 400 that may be generated using beam manipulator 130 and that beam manipulator 130 may be used to generate, for example, patterns that are more complex or less complex than pattern 400.

In spectrometer 100, a pattern may be generated on sample 155 by positioning prism 135a and/or prism 135b to deflect incident light generated by light source 125 to cause the incident light to be focused at a first point 157 of the pattern on sample 155 for a first period of time. Afterwards, prism 135a and/or prism 135b may be positioned to deflect incident light generated by light source 125 to cause the incident light to be focused at a second point 157 of the pattern on sample 155 for a second period of time. Afterwards, prism 135a and/or prism 135b may be positioned to deflect incident light generated by light source 125 to cause the incident light to be focused at a third point 157 of the pattern on sample 155 for a third period of time and so on. This technique may continue until the incident light has, for example, illuminated all desired points of the pattern. Prism 135a and/or prism 135b may also be kept in motion to illuminate all desired points of the pattern on sample 155 in a continuous fashion.

For spectrometer 100, the period of time that the incident light remains focused at a particular point on the sample may be predetermined based on various criteria. For example, the period of time may be determined based on obviating one or more undesirable effects. Here, for example, if an undesirable effect includes detonation or deflagration of the substance, the period of time may be a predetermined period of time that is less than a period of time that may cause detonation or deflagration of the substance. Note that other criteria may be used to determine the period of time.

It should be also noted that the period of time may be varied. For example, the period of time may be adjusted based on various conditions (e.g., an intensity of the incident light, an amount of scattered light detected by detector 105). In another example, the period of time may be varied from point to point. For example, in the above example, the first period of time, the second period of time, and the third period of time may all be different.

The foregoing description of embodiments is intended to provide illustration and description, but is not intended to be exhaustive or to limit the invention to the precise form disclosed. Modifications and variations are possible in light of the above teachings or may be acquired from practice of the invention.

No element, act, or instruction used herein should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

It is intended that the invention not be limited to the particular embodiments disclosed above, but that the invention will include any and all particular embodiments and equivalents falling within the scope of the following appended claims.

What is claimed is:

1. An apparatus comprising:
   a light source for generating an incident light at a first frequency;
   a beam manipulator having a polyhedron-shaped prism and a drive mechanism for positioning the prism, a position of the prism being adjustable by the drive mechanism to deflect the incident light for focus along an offset focus path at a plurality of points on a sample to form a pattern on the sample; and
   an optical component that:
     collects the deflected incident light;
     focuses the collected deflected incident light at the plurality of points on the sample, and
     collects scattered light from the sample, the scattered light including elastic scattered light and inelastic scattered light, the inelastic scattered light having a second frequency that is shifted up or down from the first frequency.

2. The apparatus of claim 1 further comprising:
   a detector having circuitry for:
   detecting the inelastic scattered light.

3. The apparatus of claim 2, further comprising:
   an analyzer for:
     identifying a substance contained in the sample based on the detected inelastic scattered light.

4. The apparatus of claim 1, wherein the drive mechanism is belt driven, gear driven, or shaft driven.

5. The apparatus for claim 1, wherein the drive mechanism includes a motor and a component driven by the motor.

6. The apparatus of claim 1, wherein the polyhedron-shaped prism is a wedge-shaped prism.

7. An apparatus comprising:
   a light source having circuitry for generating an incident light at a first frequency;
   a beam manipulator having a wedge-shaped refracting optical component and a drive mechanism for positioning the wedge-shaped refracting optical component, a position of the refracting optical component being adjustable by the drive mechanism to deflect the incident light for focus along an offset focus path at a plurality of points on a sample to form a pattern on the sample; and
   an optical component that:
     collects the deflected incident light;
     focuses the collected deflected incident light at the plurality of points on the sample, and
     collects scattered light from the sample, the scattered light including elastic scattered light and inelastic scattered light, the inelastic scattered light having a second frequency that is shifted up or down from the first frequency.

8. The apparatus of claim 7 further comprising:
   a detector having circuitry for:
   detecting the inelastic scattered light.

9. The apparatus of claim 7, wherein the drive mechanism is belt driven, gear driven, or shaft driven.

10. The apparatus of claim 7, wherein the drive mechanism includes a motor and a component driven by the motor.

11. The apparatus of claim 10, wherein the component driven by the motor is a gear, belt, or shaft.

* * * * *